United States Patent [19]

Sequeira

[11] Patent Number: 4,834,980

[45] Date of Patent: May 30, 1989

[54] TRANSDERMAL DELIVERY OF AZATIDINE

[75] Inventor: Joel A. Sequeira, New York, N.Y.

[73] Assignee: Schering Corporation, Kenilworth, N.J.

[21] Appl. No.: 102,233

[22] Filed: Sep. 28, 1987

Related U.S. Application Data

[63] Continuation of Ser. No. 838,868, Mar. 12, 1986, abandoned, which is a continuation-in-part of Ser. No. 633,541, Jul. 23, 1984, abandoned.

[51] Int. Cl.$^4$ .................. A61K 9/06; A61L 15/03; A61F 13/00
[52] U.S. Cl. .................. 424/449; 514/886; 514/887; 514/944; 514/946; 514/969; 514/316; 514/318
[58] Field of Search ............. 424/449; 514/886, 887, 514/944, 946, 969, 316, 318

[56] References Cited

U.S. PATENT DOCUMENTS

| 3,301,863 | 1/1967 | Villani | 260/293 |
|---|---|---|---|
| 3,326,924 | 6/1967 | Villani | 546/93 |
| 3,357,986 | 12/1967 | Villani | 260/293 |
| 3,366,635 | 1/1968 | Villani | 260/290 |
| 3,419,565 | 12/1968 | Villani | 260/294.7 |
| 3,435,114 | 3/1969 | Lish et al. | 424/247 |
| 3,573,297 | 3/1971 | Lish et al. | 260/293 |
| 4,355,036 | 10/1982 | Villani | 514/316 |
| 4,454,143 | 6/1984 | Villani | 514/318 |
| 4,466,953 | 8/1984 | Keith et al. | 424/28 |
| 4,470,962 | 9/1984 | Keith et al. | 424/28 |
| 4,472,372 | 9/1984 | Keith et al. | 424/19 |
| 4,560,688 | 12/1985 | Villani | 514/243 |
| 4,602,099 | 7/1986 | Parker | 549/479 |

Primary Examiner—Shep K. Rose
Attorney, Agent, or Firm—Anita W. Magatti; James R. Nelson; Stephen I. Miller

[57] ABSTRACT

Compositions for the transdermal delivery of azatadine and the use of such compositions in the treatment of allergic reactions are disclosed.

18 Claims, No Drawings

TRANSDERMAL DELIVERY OF AZATIDINE

The present application is a continuation of U.S. application Ser. No. 838,868, filed Mar. 12, 1986, now abandoned, which is a continuation-in-part of U.S. application Ser. No. 633,541, filed July 23, 1984, now abandoned.

BACKGROUND OF THE INVENTION

The present invention relates to the transdermal administration of a pharmacological agent, namely, azatadine.

In recent years, various drug delivery systems have been developed which provide sustained release therapy via a sub-dermal insert. Systems have been disclosed which also provide drug delivery systems suitable for transdermal drug administration.

U.S. Pat. No. 4,336,243 discloses a transdermal delivery pad for nitroglycerin administration, and which utilizes a hydrophobic solvent to enhance nitroglycerin dispersion and transport.

Azatadine, 6,11-dihydro-11-(1-methyl-4-piperidylisene)-5H-benzol[5,6]-cyclohepta[1,2-b]pyridine, clinically effective for treating various allergic reactions. Currently, the only form of dosage of azatadine commercially available is the oral form. While a local anesthetic effect by topical application of a 0.5% azatadine solution is mentionefd in Yanagida et al., *CIEA Preclinical Rep.*, 1, 79-89 (Feb. 1975) and intranasal application of azatadine is mentioned in Naclerio et al., *Allergy Clin. Immunol.*, 71:89, Jan. 1983 (Supplement) (Part 2) (Abstract 4); Norman, P.S., *J. Allergy Clin. Immunol.*, 72:421-32, Nov. 1983 (Part 1); and Naclerio et al., *Arch. Otolarynol.*, 110:25-7, Jan. 1984; none of these articles indicate that any systemic antihistaminic or anti-allergic effect could be obtained by transdermal delivery of azatadine.

SUMMARY OF THE INVENTION

The present invention provides a transdermal delivery system for the administration of azatadine and/or its salt forms, and more specifically provides a method and a composition wherein a transdermal device, hereinafter referred to as a patch, is conveniently applied to the skin to provide transdermal azatadine administration over a prolonged period of time. Thus, the method, composition and patch of the invention can be used to provide systemic treatment of allergic reactions remote to the site of application, i.e., the anti-allergic activity can be provided by distribution of azatadine via the blood rather than by local anti-allergic activity at the site of application of the azatadine transdermal composition and/or patch.

The use of transdermal drug delivery systems produces more controlled blood levels, lower frequency of dosing and enhanced patient compliance. Further, the transdermal delivery of an antihistamine to treat various allergic reactions is most desireable for reasons of convenience and effectiveness.

It is true, however, that not all antihistamines possess the properties necessary to be effective in a transdermal drug delivery system. These properties are high potency, proper physico-chemical characteristics, good dermal penetration and lack of dermal irritation and/or sensitization.

Quite unexpectedly, azatadine has been found to possess all of the above described properties which are necessary for being effective in a transdermal drug delivery system. Frequently, in order to obtain effective dermal penetration of drugs in a transdermal delivery system, a promoter such as dimethyl sulfoxide is used. It is unexpected that azatadine's transdermal effectiveness is not dependent on the use of such a promoter.

In addition, anti-allergic pharmaceuticals tend to cause sedative side effects. This is also true for azatadine when taken orally. It is expected, however that the administration of azatadine via low concentration transdermal formulations will eliminate or reduce the side effects of drowsiness and/or sedation as compared to oral administration. This decrease in sedative side effects is expected despite the relatively high blood levels of azatadine that are provided by transdermal administration in accordance with the invention. Also, in comparison to oral administration, transdermally administered azatadine provides higher urinary levels of unmetabolized azatadine, which indicates that a lower transdermal dose may be as effective as the usual oral dose.

The invention sought to be patented in its method aspect is a pharmaceutical method for the systemic treatment of allergic reactions in a mammal which comprises the transdermal application of an effective amount of azatadine and a pharmaceutically acceptable transdermal carrier. The preferred mode for accomplishing the transdermal application of azatadine is via a transdermal patch.

The invention sought to be patented in a transdermally acceptable pharmaceutical dosage formulation and/or composition comprises an effective amount of azatadine and a pharmaceutically acceptable transdermal carrier. Preferably, the transdermally acceptable composition is utilized to prepare a "reservoir type" or "matrix type" patch which is applied to the skin and worn for a specific period of time to permit the penetration of a desired amount of azadadine through the skin. Most preferably, the patch of the invention wil be worn for a period of about 72-96 hours and provide a total daily dosage of about 0.1 to about 5 mg, preferably about 0.5 mg to about 1.5 mg of azatadine. The patch may then be replaced if necessary with a fresh patch, thereby providing a constant blood level of azatadine to the patient in need therefore.

DESCRIPTION OF THE INVENTION

Azatadine may be prepared by the method disclosed in U.S. Pat. No. 3,326,924. Pharmaceutically acceptable salts of azatadine such as the maleate, sulfate, succinate and acetate salts may also be prepared as described therein and these are equivalent to azatadine for purposes of the invention. A preferred pharmaceutically acceptable salt of azatadine is the maleate salt.

Azatadine is an orally acceptable antihistamine currently approved for sale in the United States and other countries of the world for use in the treatment of allergic desorders such as urticaria, seasonal rhinitis and pollen sensitivity.

In an attempt to find a transdermally effective antihistamine, various known antihistamines were evaluated for their dermal irritation and dermal penetration properties. The results of these evaluations are set forth in Table 1. The irritation results are reported as either irritating (+) or non-irritating (−), and the pentration results are reported as either good (+) or poor (−). Some antihistamines listed were not tested for in vitro dermal penetratilon and these are indicated as ---.

TABLE 1

Transdermal Application of Antihistamines

| Compound | Rabbit Dermal Irritation[a*] | In Vitro Dermal Penetration |
|---|---|---|
| Chlorpheniramine base (patch) | (+) | (+) |
| Chlorpheniramine maleate (20%) | (−) | (−) |
| Chlorpheniramine succinate (20%) | (−) | (−) |
| Chlorpheniramine sulfate (20%) | (−) | (−) |
| Chlorpheniramine acetate (20%) | (+) | (+) |
| Chlorpheniramine palmitate (20%) | (+) | (+) |
| Pheniramine base (20%) | (+) | — |
| Dexbrompheniramine (10%) | (+) | — |
| Dexchlorpheniramine base | (+) | — |
| Azatadine | (−) | (+) |
| Doxylamine succinate | (+) | — |
| Diphenhydramine HCl | (+) | — |
| Triprolidine HCl | (+) | — |
| Diphenylpyraline HCl | (+) | — |
| Cyproheptadine HCl | (−) | (−) |
| Promethazine HCl | (+) | — |
| Carbinoxamine maleate | (+) | — |
| Dimethindine maleate | (+) | — |

[a*]Results of a 24/72 hour (no irritation seen for the first 24 hours) dermal irritation screen in rabbits with intact skin.

SCREENING OF ANTHIHISTAMINE FOR DERMAL IRRITATION

Eight young adult New Zialand white rabbits were assigned to two groups. The rabbits were housed in stainless steel cages and maintained under standard laboratory conditions. Each cage was identified with a color coded lable indicating the test substance, rabbit number, sex, and study number. Food and water were supplied ad libitum. On the day of dosing, the back of each rabbit was clipped free of hair. The test substance, a 20% antihistamine formulation, or a placebo formulation was instilled into two Hill Top Chambers and affixed one on each side of the midline of the back. To prevent removal, the chambers were covered with an orthopedic stockinette and secured by a canvas coat. Signs of dermal irritation graded on the basis of criteria presented in Draize, J.H; Dermal Toxicology, An Appraisal Of The Safety And Chemical In Food Drugs & Comestics. The Association of Food & Drug Officals of the United States 1959 pp 46–59, were recorded after removal of the chambers at 24 and 72 hours.

SCREENING OF ANTIHISTAMINES FOR DERMAL PENETRATION

The skin penetration assembly used was similar to that described by Franz (J. Invest. Derm., 64:190, 1975). Excised defatted human skin was stretched across a resevoir containing a phosphate buffer solution (pH 794, 0.02M) in direct contact with the dermal side of the skin. The temperature of this buffer solution was maintained at 37±0.5° C. by circulating water at the appropriate temperature through a jacket which surrounds each assembly. Freshly made preparation was applied to the stratum corneum surface. The buffer solution was removed in its entirety and replaced with fresh solution at various time intervals and assayed for azatadine content.

Several antihistamines were eliminated from consideration as effective transdermal drugs because they were shown to be dermal irritants. Another group of antihistamines, through they showed no dermal irritation, did not show dermal penetration, the latter property being an essential requirement for the effectiveness of a transdermal drug.

The results given in Table 1 reveal that usually antihistamines which give positive results for dermal penetration are unacceptable for transdermal applications because of their dermal irritatant properties. It is surprising to find that after numerous antihistamines were tested, there was only one antihistamine, azatadine, that had good dermal penetration and no dermal irritation and/or sensitization. Thus, the results in Table 1 show that of the compounds tested for transdermal application, only azatadine possesses the characteristics necessary for transdermal use.

Although certain formulations are preferred, the use of a particular transdermal formulation is not critical to the practice of the invention in its broadest aspects. Thus, the invention contemplates the use of any formulation, including those not yet descovered or fully characterized, so long as the transdermal dosage form can be utilized to transdermally deliver the desirable amount of azatadine.

One preferred formulation for use in the invention is a cream which comprises the following components in the indicated proportions:

| Component | mg/g range |
|---|---|
| Azatadine | 5.0–250.0 |
| Mineral Oil | 25.0–100.0 |
| White petrolatum | 50.0–200.0 |
| Cetostearyl alcohol | 30.0–100.0 |
| Ceteareth-30 | 10.0–50.0 |
| Propylene glycol | 50.0–200.0 |
| Water q.s. ad | 1.0 g |

However, it should be noted that other formulations such as lotions, ointments and gels may also be employed.

It is of interest to the practice of the present invention that the total daily dosage (through the skin) of azatadine which is administered by the transdermal formulation may be less than the currently recommended clinical daily dose administered by the oral route. Moreover, it is anticipated that upon implementation of the invention the azatadine blood levels will be more consistent and controlled than those obtained upon oral administration of the drug. However, this is not a requirement of the invention. This feature is anticipated in view of clinical experience with other transdermal drugs. Thus, the total daily transdermal dosage of azatadine when administered in a patch is expected to be from about 0.1 mg to about 5.0 mg, with 0.5 mg to about 1.5 mg being preferred. The particular dosage may be varied depending on the size and age of the patient and may also depind upon the severity of the condition being treated. Such dosage modification is within the skill of the clinical arts. The utilization of this new dosage form and its prescribed regimen will provide the recongnized clinical efficacy of azatadine, having the advantages described above. Other frequencies of dosage application are anticipated, for example, a once every 3 day frequency or a once every 7 day frequency. Although a twice a week dosage regimen may be preferred, it is not intdnded that the invention be·limited to any particular regimen.

Table 2 contains in vitro skin diffusion flux results obtained using human cadaver skin in a Franz diffusion cell, for a 1 $cm^2$ area. Flux is defined as the amount of drug that traverses skin over time for a specified area.

TABLE 2

| Formulation[a] | Accumulative Azatadine (mg/per cm$^2$) | | |
|---|---|---|---|
| | 20 Hr | 45 Hr | 72 Hr |
| Ointment A | 2.10 | 7.54 | 13.83 |
| Ointment B | 3.24 | 10.16 | 17.38 |
| Cream | 3.01 | 13.69 | 27.41 |
| Gel | 2.38 | 7.11 | 11.79 |

[a]Prepared in Examples 1-4, respectively

This data (Table 2) indicates that azatadine traverses human skin in amounts which are clinically effective. The transdermal dose for clinical effectiveness is expected to be 1 mg/day. Azatadine flux rates of greater than 1 mg day (the preferred daily clinical dosage) were achieved within 20 hours for all of the formulations evaluated (Table 2). Those flux rates achieved a steady-state level between 20-45 hours post patch application. Moreover, these high flux rates were achieved without the use of promotants (e.g., dimethyl sulfoxide). The following examples illustrate formulations of azatadine that show good dermal penetration.

EXAMPLE 1

| Ointment A | mg/g |
|---|---|
| Azatadine | 100 |
| White Petrolatum | 900 |

EXAMPLE 2

| Ointment B | mg/g |
|---|---|
| Azatadine | 50 |
| Propylene glycol | 200 |
| White Petrolatum | 750 |

EXAMPLE 3

| Cream | mg/g |
|---|---|
| Azatadine | 100 |
| Mineral Oil | 48 |
| White Petrolatum | 120 |
| Cetostearyl Alcohol | 57.6 |
| Polyethylene glycol 1000 monocetylether | 18.0 |
| Propylene glycol | 80 |
| Water | 576.4 |

EXAMPLE 4

| Gel | mg/g |
|---|---|
| Azatadine | 100 |
| Pluronic F-127 | 250 |
| Ethanol | 200 |
| Water | 450 |

EXAMPLE 5

| Cream | A mg/g | B mg/g |
|---|---|---|
| Azatadine | 100.00 | 25.0 |
| Mineral Oil | 54.0 | 54.0 |
| White Petrolatum | 135.0 | 135.0 |
| Cetostearyl Alcohol | 65.0 | 65.0 |
| Ceteareth-30 | 20.0 | 20.0 |
| Propylene Glycol | 100.0 | 100.0 |
| Water q.s. ad | 1.0 g | 1.0 g |

The formulations of Examples 1-5 can be packaged to produce a "reservoir type" transdermal patch with or without a rate-limiting patch membrane. The size of the patch and or the rate limiting membrane can be chosen to deliver the transdermal flux rates desired. Such a transdermal patch can consist of a polypropylene/polyester impervious backing member heat-sealed to a polypropylene porous/permeable membrane with a reservoir therebetween. The patch can include a pharmaceutically acceptable adhesive (such as a acrylate, silicone or rubber adhesive) on the membrane layer to adhere the patch to the skin of the host, e.g., a mammal such as a human. A release liner such as a polyester release liner can also be provided to cover the adhesive layer prior to application of the patch to the skin as is conventional in the art. This patch assembly can be paclaged in an aluminum foil or other suitable pouch, again as is conventional in the art.

Alternatively, azatadine and or its salts can be formulated into a "matrix-type" transdermal patch as in Examples 6 and 7. Drug Delivery Systems Characteristics and Biomedical Application, R. L Juliano, ed., Oxford University Press. N.Y. (1980); and Controlled Drug Delivery Vol.I Basic Concepts, Stephen D. Bruck (1983) describe the theory and application of methods useful for transdermal delivery systems. The relevant teachings of these texts are herein incorporated by reference. The drug-matrix could be formed utilizing various polymers, e.g. silicone, polyvinyl alcohol The "drug matrix" may then be packaged into an appropriate transdermal patch.

A third type of patch comprises incorporating the drug directly in a pharmaceutically acceptable adhesive and laminating the drug-containing adhesive onto a suitable backing member, e.g. a polyester backing membrane. The drug should be present at a concentration which will not affect the adhesive properties, and at the same time deliver the required clinical dose.

EXAMPLE 6

| Patch | mg/g |
|---|---|
| Azatadine | 100 |
| silicone polymer | 900 |

EXAMPLE 7

| Patch | mg/g |
|---|---|
| Azatadine | 200 |
| Polyvinyl alcohol polymer | 800 |

EXAMPLE 8

| Patch | mg/patch |
|---|---|
| Azatadine | 10 |

| -continued | |
|---|---|
| Patch | mg/patch |
| Avery I-780 adhesive | * |

*a quantity sufficient to incorporate the drug without loss of adhesive properties.

The invention also contemplates a package which contains a specfic number of transdermal patched that may be utilized to complete a specified course of treatment. For example a package containing several patches would be utilized to complete a course of therapy, e.g. two 96-hour patches for an eight day course of therapy.

While the present invention has been described in connection with certain embodiments, many alternatives, modifications and variations will be apparent to those of ordinary skill in the art in light of the foregoing description. Accordingly, all such alternatives, modifications and variations are intended to be included within the present invention.

I claim:

1. A method for treating allergic reactions in a mammal consisting essentially of the transdermal application of a non-dermally irritating, anti-allergic effective amount of azatadine or a pharmaceutically acceptable salt thereof and a pharmaceutically acceptable transdermal carrier.

2. A transdermally acceptable pharmaceutical composition consistine essentially of a non-dermally irritating, anti-allergic effective amount of azatadine or a pharmaceutically acceptable salt thereof and a pharmaceutically acceptable transdermal carrier.

3. The composition defined in claim 2 which is formulated as an ointment.

4. The ointment defined in claim 3 consisting essentially of 100 mg of azatadine and 900 mg of white petrolatum per gram of ointment.

5. The ointment defined in claim 3 consisting essentially of 50 mg of azatadine, 200 mg of propylene glycol and 750 mg of white petrolatum per gram of ointment.

6. The composition defined in claim 2 which is formulated as a cream.

7. The cream defined in claim 6 consisting essentially of the following components in the indicated proportions per 1 gram of said cream: from about 5 to about 250 mg of azatadine, from about 25 to about 100 mg of mineral oil, from about 50 to about 200 mg of white petrolatum, from about 30 to about 100 mg of cetostearyl alcohol, from about 10 to about 50 mg of Ceteareth-30, from about 50 to about 200 mg of propylene glycol, with the remainder comprising water.

8. The cream defined in claim 6 consisting essentially of 100 mg of azatadine, 48 mg of mineral oil, 120 mg of white petrolatum, 57.6 mg of cetostearyl alcohol, 18 mg of polyethylene glycol 1000 monocetyl ether, 80 mg of propylene glycol and 576.4 mg of water.

9. The cream defined in claim 7 consisting essentially of the following components in the indicated proportions per gram of said cream: 25 mg of azatadine, 54 mg of mineral oil, 135 mg of white petrolatum, 65 mg of cetostearyl alcohol, 20 mg of Cetareth-30, 100mg of propylene glycol, with the remainder consisting essentially of water.

10. The composition defined in claim 2 which is formulated as a gel.

11. The geldefined in claim 8 consisting essentially of 100 mg of azatadine, 250 mg of pluronic F-127, 200 mg of ethanol and 450 mg of water per gram of gel.

12. The composition defined in claim 2 in the form of a transdermal patch.

13. The composition of claim 12 wherein the transdermal patch comprises a cream consisting essentially of the following components per gram of said cfream: 25 mg of azatadine, 54 mg of mineral oil, 135 mg of white petrolatum, 65 mg of cetostearyl alcohol, 20 mg of Cetareth-30, 100 mg of propylene glycol, with the remainder consisting essentially of water.

14. The composition of claim 12 wherein the transdermal patch comprises a matrix consisting essentially of 100 mg azatadine and 900 mg of silicone polymer per gram of matrix.

15. The composition of claim 12 wherein the transdermal patch consisting essentially a matrix comprised of 200 mg azatadine and 800 mg of polyvinyl alcohol polymer per gram of matrix.

16. The composition of claim 12 wherein the transdermal patch consists essentially of a non-dermally erritating, anti-allergy effective amount of azatadine in a pharmaceutically acceptable adhesive.

17. The method of claim 1 wherein 0.1 to 5 mg of azatadine penetrates the skin of said mammal in a 24-hour period.

18. The method of claim 17 wherein 0.5 to 1.5 mg of azatadine penetrates the skin of said mammal in a 24-hour period.

* * * * *